United States Patent [19]

Kuberasampath et al.

[11] Patent Number: 5,171,574

[45] Date of Patent: * Dec. 15, 1992

[54] BONE COLLAGEN MATRIX FOR IMPLANTS

[75] Inventors: Thangavel Kuberasampath, Medway; Richard J. Ridge, Acton, both of Mass.

[73] Assignee: Stryker Corporation, Kalamazoo, Mich.

[ * ] Notice: The portion of the term of this patent subsequent to Nov. 10, 2009 has been disclaimed.

[21] Appl. No.: 483,913

[22] Filed: Feb. 22, 1990

Related U.S. Application Data

[63] Continuation-in-part of Ser. No. 422,613, Oct. 17, 1989, Pat. No. 4,975,526, which is a continuation-in-part of Ser. No. 315,342, Feb. 23, 1989, Pat. No. 5,011,691.

[51] Int. Cl.$^5$ .............................. A61F 2/02; C08J 3/12; C08L 89/04; C07K 3/28
[52] U.S. Cl. .................................. 424/423; 424/424; 424/426; 523/113; 530/356; 530/840; 128/DIG. 8
[58] Field of Search ........................ 424/423, 424, 426; 523/113; 530/356, 350, 402, 412, 427, 840; 128/DIG. 8

[56] References Cited

U.S. PATENT DOCUMENTS

| | | | |
|---|---|---|---|
| 4,172,128 | 10/1979 | Thiele et al. | 424/95 |
| 4,394,370 | 7/1983 | Jefferies | 424/15 |
| 4,563,350 | 1/1986 | Nathan et al. | 424/15 |
| 4,563,489 | 1/1986 | Urist | 524/21 |
| 4,657,548 | 4/1987 | Nichols | 623/10 |
| 4,703,108 | 10/1987 | Silver et al. | 530/356 |
| 4,725,671 | 2/1916 | Chu et al. | 530/356 |
| 4,789,663 | 12/1988 | Wallace et al. | 514/21 |
| 4,795,467 | 1/1989 | Piez et al. | 623/16 |
| 4,812,120 | 3/1989 | Flanagan et al. | 433/173 |
| 4,837,285 | 6/1989 | Berg et al. | 530/356 |

FOREIGN PATENT DOCUMENTS

| | | |
|---|---|---|
| 069260 | 6/1982 | European Pat. Off. . |
| 0148155 | 1/1985 | European Pat. Off. . |
| 0169001 | 7/1985 | European Pat. Off. . |
| 1709796 | 7/1985 | European Pat. Off. . |
| 0182483 | 10/1985 | European Pat. Off. . |
| 0212474 | 8/1986 | European Pat. Off. . |
| 0230647 | 8/1987 | European Pat. Off. . |
| 0309241 | 9/1988 | European Pat. Off. . |
| 8600526 | 1/1986 | PCT Int'l Appl. . |
| 8800205 | 1/1988 | PCT Int'l Appl. . |
| 2178447 | 2/1987 | United Kingdom . |

OTHER PUBLICATIONS

"Application of the Biological Principle . . . ", Glowicki et al., The Lancet, pp. 959-963, (May 2, 1981).
"Cell Biology and Biochemistry of Endochondral Bone Development", Reddi, Coll. Res. 1: pp. 209-226, (1981).
"Dissociative Extraction and Reconstitution . . . ", Sampath et al., 78 Proc. Natl. Acad. USA (12), pp. 7599-7603, (Dec. 1981).
"Homology of Bone-Inductive Proteins . . . ", Sampath et al., Proc. Natl. Acad. Sci. USA 80: pp. 6591-6595, (Nov. 1983).

(List continued on next page.)

Primary Examiner—Nathan M. Nutter
Attorney, Agent, or Firm—Testa, Hurwitz & Thibeault

[57] ABSTRACT

A matrix for implantation in a mammalian host comprising biocompatible, mineral-free, insoluble Type-I bone collagen which may be allogenic or xenogenic to the host, and which, when implanted in the host, is biodegradable. The collagen is treated with a collagen fibril modifying substance such as acidified acetonitrile, chloroform, or dichloromethane, or by heating in an aqueous environment to a temperature of 37°-65° C. The treated material undergoes a change in morphology involving a significant increase in its surface area as measured by various methods. Under the scanning electron microscope the material has an "oyster shell" appearance with many pits and micropores.

29 Claims, 11 Drawing Sheets

OTHER PUBLICATIONS

"A Modified Perfusion-Microcarrier . . . ", Strand et al., Biotech. Bioeng. 26: pp. 503–507, (1984).

"β-Tricalcium Phosphate Delivery System for Bone Morphogenetic Protein", Urist et al., Clin. Orthoped. Rel. Res. 187: pp. 277–280, (1984).

"Packaging and Delivery of Bone Induction Factors in a Collagenous Implant", Deatherage et al., Collagen Rel. Res. 7: pp. 225–231, (1987).

"Historical Review of Porous-coated Implants", Spector, J. Arthroplasty 2: pp. 163–177, (1987).

"Failure of Bone Induction by Bone Matrix in Adult Monkeys", Aspenberg et al., J. Bone Joint Surg. [BR] 70: pp. 625–627, (1988).

"Hydroxyapatite-Coated Titanium for Orthopedic Implant Application", Cook et al., Clin. Orthopaed. Rel. Res. 232: pp. 225–243, (1988).

"A Review of Matrix-Induced Osteogensis . . . ", Deatherage et al., Int. J. Oral Macillofac. Surg. 17: pp. 395–399, (1988).

BONE COLLAGEN MATRIX FOR IMPLANTS

REFERENCE TO RELATED APPLICATIONS

This application is a continuation-in-part of copending U.S. Pat. application Ser. No. 422,613, filed Oct. 17, 1989, now U.S. Pat. No. 4,975,526, which is a continuation-in-part of copending U.S. Pat. application Ser. No. 315,342 filed Feb. 23, 1989 entitled Osteogenic Devices now U.S. Pat. No. 5,011,691 the disclosures of which are hereby incorporated by reference.

BACKGROUND OF THE INVENTION

This invention relates to a biocompatible, implantable material which is absorbed naturally in vivo with minimal immunological reaction, and to the methods for its production. More particularly, this invention relates to a novel collagenous bone matrix useful as an allogenic or xenogenic implant for use as an osteogenic device, as a bone particle coating for implantable prostheses, as a delivery vehicle for the in vivo sustained release of protein, and as a substratum for growth of anchorage-dependent cells.

A biocompatible, implantable material that can be resorbed in vivo could be used to promote conductive bone growth, induce osteogenesis when combined with an osteoinductive protein, provide a substratum for in vivo or in vitro growth of anchorage-dependent cells, or serve as a carrier for the sustained release of, for example, a therapeutic drug or antibiotic. Such a material must be biocompatible, that is, must not induce an immunogenic or continued inflammatory response in vivo. Its physical structure must allow cell infiltration, and it must have an in vivo resorption time appropriate for its function.

The potential utility of an osteogenic device capable of inducing endochondral bone formation in vivo has been recognized widely. It is contemplated that the availability of such devices would revolutionize orthopedic medicine, certain types of Plastic surgery, and various periodontal and craniofacial reconstructive procedures.

The developmental cascade of bone differentiation induced by the implantation of demineralized/bone matrix is well documented in the art (Reddi, 1981, *Collagen Rel. Res.* 1:209-226). Although the precise mechanisms underlying the phenotypic transformations are unclear, it has been shown that the natural endochondral bone differentiation activity of bone matrix can be dissociated into two principle components: a soluble proteinaceous component responsible for osteogenic activity, and an insoluble collagenous matrix (residue serves as a carrier for bone induction). The soluble osteoinductive protein components are then reconstituted with inactive residual collagenous matrix to restore full bone inducing activity (Sampath et al., *Proc. Natl. Acad. Sci. USA* 7599-7603 (1981). Recently, the protein factors hereafter referred to as osteogenic protein (OP) responsible for inducing osteogenesis have been purified, expressed in recombinant host cells, and shown to be truly osteoinductive when appropriately sorbed onto allogenic demineralized bone powder. (U.S. Pat. application Ser. No. 179,406 now U.S. Pat. No. 4,968,590.

Studies have shown that while osteoinductive proteins are useful cross species, the collagenous bone matrix generally used for inducing endochondral bone formation is species specific (Sampath and Reddi (1983) PNAS 80:6591-6594). Implants of demineralized, delipidated, extracted xenogenic bone matrix as a carrier in an in vivo bone induction system invariably has failed to induce osteogenesis, presumably due to inhibitory or immunogenic components in the bone matrix. However, even the use of allogenic bone matrix in osteogenic devices may not be sufficient for osteoinductive bone formation in many species. For example, allogenic, subcutaneous implants of demineralized, delipidated monkey bone matrix is reported not to induce bone formation in the monkey. (Asperberg et al., *J. Bone Joint Suro.* (Br) 70-B:625-627 (1988)).

U.S. Pat. No. 4,563,350, published Jan. 7, 1986, discloses the use of trypsinized bovine bone matrix as a xenogenic matrix to effect osteogenic activity when implanted with extracted partially purified bone inducing protein preparations. Bone formation is said to require the presence of at least 5%, and preferably at least 10%, non-fibrillar collagen in the disclosed matrix. The authors claim that removal of telopeptides which are responsible in part for the immunogenicity of collagen preparations is more suitable for xenogenic implants.

EPO 309,241 (published 3/29/89, filed 9/22/88, priority 9/25/87) discloses a device for inducing endochondral bone formation comprising an osteogenic protein preparation, and a matrix carrier comprising 60-98% of either mineral component or bone collagen powder and 2-40% atelopeptide hypoimmunogenic collagen.

Deatherage et al., (1987) *Collagen Rel. Res.* 7:2225-2231, purport to disclose an apparently xenogenic implantable device comprising a bovine bone matrix extract that has been minimally purified by a one-step ion exchange column and reconstituted highly purified human Type-I placental collagen.

In order to repair bone defects in orthopedic reconstructive surgery, biomaterials based on collagens, minerals/ceramics, polymers and metal implants are being used as implants. These biomaterials are known to support healing by conduction but do not induce new bone. The current state of the art of materials used in surgical procedures requiring conductive bone repair, such as the recontouring or filling in of osseous defects, is disclosed by Deatherage (1988) *J. Oral Maxillofac. Surg.* 17:395-359. All of the known implant materials described (hydroxylapatite, freeze-dried bone, or autogenous bone grafts) have little or no osteoinductive properties. The ability to induce osteogenesis is preferred over bone conduction for most procedures.

U.S. Pat. No. 4,795,467 discloses a bone repair composition comprising calcium phosphate minerals (preferable particle size of 100-2,000µ) and atelopeptide, reconstituted, crosslinked, fibrillar collagen. It purports to be a non-antigenic, biocompatible, composition capable of filling bony defects and promoting bone growth xenogenically.

U.S. Pat. No. 4,789,663 discloses using xenogenic collagen from bone and/or skin to effect conductive bone repair by exposing the defect to fresh bone, wherein the collagen is enzymatically treated to remove telopeptides, and is artificially crosslinked.

In order to enhance bone ingrowth in fixation of orthopedic prostheses, porous coatings on metallic implants are being employed. Although the surface chemistry of porous coatings plays a role in bone conduction, it appears bone has higher tensile and shear strength and higher stiffness at the porous coating - bone interface.

The need to provide a "biological anchor" for implanted prostheses, particularly metallic implants, is well documented in the art. The state of the art of prosthetic implants, disclosed by Specter (1987) *J. Arthroplasty* 2:163-177, generally utilizes porous coated devices, as these coats have been shown to promote cellular ingrowth significantly.

Recently the art also has sought to increase cellular ingrowth of implanted prostheses by coating their surfaces with collagen preparations. For example, EPO 169,001 (published 1/22/86) claims a collagen-coated prosthesis wherein the coat comprises a purified, sterile, non-immunogenic xenogenic collagen preparation from bone or skin. The collagen is preferably atelopeptide collagen. The coating is formed by dipping the prosthesis into a suspension of collagen, or forming a collagen sheet that is wrapped about the prosthesis.

U.S. Pat. No. 4,812,120 discloses a prosthetic device comprising a metal core over which are applied successive polymer layers. The outer layer comprises a biopolymer having protruding collagen fibrils. The protruding fibrils are subject to damage upon implantation of the device. Increased surface area and pore size in a matrix has been shown to enhance cell attachment and growth of anchorage-dependent cells in vitro.

Efficient in vitro growth of mammalian cells is often limited by the materials used as the substratum or "scaffold" for anchorage-dependent cells. An optimal matrix for this purpose must be physiologically acceptable to the anchorage dependent cells, and it must also provide a large available surface area to which the cells can attach. GB U.S. Pat. No. 2,178,447, published Feb. 11, 1987, discloses a fibrous or porous foam matrix comprising open or closed form fibers, with a pore size on the order of 10-100μm (matrix height is 50-500μ). The fiber network is generated as a sheet which must then be modified if different scaffold shapes are desired. Strand et al. (Biotechnology and Bioengineering, V. 26, 503, 1984) disclose microcarrier beads for use as a matrix for anchorage dependent cells in a matrix perfusion cell culture. Bead materials tested were DEAE or polyacrylamide. Surface area available was 250-300 cm$^2$/g and required a cell innoculation of 10$^6$ cells/ml. U.S Pat. No. 4,725,671 claims collagen fiber membranes suitable for cell culture, comprising soluble atelopeptide collagen fibers that are dried and preferably cross-linked.

The art has sought sustained release vehicles with known, reliable "release" rates. Effective carriers must be biocompatible, water-insoluble, capable of trapping or otherwise holding the therapeutic agent of interest for a required time, and must have a resorption time in vivo that mimics the desired release rate of the agent. Collagens are attractive carriers for clinical use, primarily because of their biocompatible and biodegradable properties. The carriers are generally formulated into "sponge-like" structures by solubilizing or dispersing collagen and then solidifying the solution so that monofilaments are captured in a generally, random, open-structured array. The solvent is then removed, and the molecules chemically crosslinked to maintain the open-structure and render the carrier water insoluble. The therapeutic compound is preferably mixed with the collagen in solution prior to solidification.

The structures can be made in a variety of shapes. For example, EPO 230,647, published Aug. 5, 1987, discloses structures formed as micropellets. The structures can also be made in sheet form (U.S. Pat. No. 4,703,108, published,, Oct. 27, 1987), rods or tubes (see, for example, EPO 069,260, published Jan. 12, 1983, EPO 170,979, published Feb. 12, 1986, and U.S 4,657,548, published Apr. 14, 1987), or beads. U.S. Pat. No. 4,837,285, published Jun. 6, 1989, discloses a composition for wound dressings or drug delivery systems made of porous beads formed by freeze-drying microdroplets containing the agent of interest and solubilized or dispersed Type I or Type III collagen. The microdroplets are then slowly lyophilized or air-dried to form beads which are then crosslinked.

Unfortunately, the high "fiber-forming" property of collagen can interfere with the formation of uniform and homogeneous solutions, making efficient synthesis of appropriate carrier matrices difficult. In addition, the use of crosslinking agents (e.g., glutaraldehyde) may have adverse biological effects, such as cell cytotoxicity (Cooke, et al. *British J. Exo. Path.* 64. 172, 1983).

It is an object of this invention to provide a biocompatible, in vivo biodegradable bone matrix, implantable in a mammalian host with little or no significant inhibitory or immunogenic response. Another object is to provide a biocompatible, in vivo biodegradable matrix capable in combination with an osteoinductive protein of producing endochondral bone formation in mammals, including humans. Still other objects are to provide a superior material for coating implantable prosthetic devices, to increase the cellular ingrowth into such devices, to provide a biocompatible, in vivo biodegradable matrix for use as a carrier of sustained-release pharmaceutical compositions, wherein the resorption rate of the matrix can be adjusted to match that of the pharmaceutical agent, and to provide a biocompatible, in vivo biodegradable matrix capable of acting as a scaffold or substratum for anchorage-dependent cells, wherein the surface area available for cell attachment can be adjusted. Yet another object of the invention is to provide a method for the production of such matrix material.

These and other objects and features of the invention will be apparent from the description, drawings, and claims that follow. As used herein, "bone collagen matrix" or "bone matrix" is intended to mean stripped, cleaned and demarrowed, pulverized, delipidated bone that has been demineralized and protein extracted with guanidine hydrochloride or an equivalent extractant. "Implantable", as used herein, includes surgical introduction as well as topical application, and introduction by injection.

SUMMARY OF THE INVENTION

This invention involves a matrix for implantation in a mammalian host comprising biocompatible, mineral-free, delipidated, insoluble Type-I bone collagen which may be allogenic or xenogenic to the host, and which, when implanted in the host, is biodegradable and can serve as a substratum to support mesenchymal cell migration and proliferation. As disclosed herein, the matrix may be combined with osteogenic protein to induce endochondral bone formation reliably and reproducibly in a mammalian body. It may also be used as a surface coat around implantable prosthetic devices to promote cellular ingrowth. It can act as a carrier for the sustained release of various compositions in the mammalian body, and can provide a biocompatible substrate for anchorage-dependent cells.

The development of this matrix material resulted from the discovery of key features required for successful implantation of xenogenic bone matrix and osteogenic protein. Studies indicated that osteogenic devices comprising substantially pure osteogenic protein and allogenic demineralized, delipidated guanidine-extracted bone matrices must have interstices dimensioned to permit the influx, proliferation and differentiation of migratory cells. It was also observed that osteogenic devices comprising xenogenic bone matrices induce little or no endochondral bone formation in vivo. The absence of bone formation by xenogenic matrices generally has been thought to be due to an immunogenic or inhibitory response to protein components still present in the matrix (either the collagen telopeptides or associated non-collagenous glycoproteins.)

It has now been discovered that the overall specific surface area (surface area/unit mass), degree of porosity and micropitting, and the size of the micropits and pores of the matrix is important for successful xenogenic implants, and even for allogenic implants of certain species.

Panels A and B of FIGS. 1 and 2 are scanning electron micrographs showing the particle structure of demineralized, guanidine-extracted bone matrix from rat and calf, respectively. As can be seen from the SEMs, there is a significantly greater inherent porosity, or surface area, in rat bone matrix than in bovine bone matrix. It has been discovered that increasing porosity and intraparticle surface area of bone matrix can promote osteogenic induction as evidenced by rat collagenous bone matrix implants. This is achieved by treating collagenous bone matrix with certain solvents or heat so as to alter its morphology. Agents suitable for this purpose are disclosed herein and are termed collagen fibril modifying agents.

In one aspect, this invention comprises a matrix for implantation in a mammalian host comprising biodegradable, biocompatible mineral-free, delipidated, insoluble Type-I bone collagen, allogenic or xenogenic to the host, depleted in non-collagenous proteins, preferably in the form of particles having a mean diameter within the range of 70μm-850μm, and having an increased surface area relative to untreated material.

The treated matrix material has an increased intrusion volume, preferably at least 25% greater, and often 50% or more of untreated material; an increased number of pores and micropits; and surface area which is at least doubled as measured by the BET method. The preferred particulate material, which may be used as a shaped, interadhered particle mass or a simple agglomeration of close-packed particles, has a particle size within the range of 150μm to 420μm.

Another aspect of this invention involves methods of treating demineralized, delipidated guanidine extracted collagenous bone matrix with a collagen fibril modifying agent so as to increase the porosity of the collagen matrix to achieve the desired increase in surface area. The matrix treatments herein described increase the porosity and micropitting of the matrix particles, thereby altering the morphology of the particles. In the preferred embodiment the surface takes on the appearance at high magnification resembling an oyster shell with superposed layers with average pore size range on the order of 1.0 to 100 microns. The effect can be achieved by treatment with acids (for example trifluoroacetic acid (TFA) or hydrogen fluoride HF) alone or preferably used to acidify organic solvents, for example, dichloromethane (DCM), acetonitrile (ACN), isopropanol (IP) and/or chloroform. All these agents are known to have protein denaturation properties and to swell insoluble collagenous protein by modifying collagen fibrils. Among these, preferred agents are DCM and ACN. The currently most preferred agents are DCM or ACN acidified with a small amount, e.g., 0.1%, of TFA. This alteration can have the effect potentially of increasing or decreasing the resorption time of the matrix in vivo. Thus, one can extend treatment times to shorten the matrix resorption rate in vivo (longer treatment times yield faster resorption rates).

The surface morphology also can be achieved by heating demineralized delipidated guanidine extracted bone collagen in water at high temperature (37°–65°, preferably 45°–60° C.) for one hour or other time sufficient to achieve the desired surface morphology. Although the mechanism is not yet clear, it is hypothesized that the heating of collagen alters collagen fibrils to result in increased in surface area. Thus bone matrix may be treated at various elevated temperatures in water (1g/30ml) with stirring and then filtered. Treatment of insoluble collagen in water by increasing temperature results initially in a melting transition (Tm), the temperature required to go from one-quarter to three quarters of the total transition from helical structure to non-helical. Thereafter the fibrils will abruptly shrink a fraction of length at some higher temperature, designated as the shrinkage temperature (Ts). Ts is normally higher then Tm, reflecting the added stability contributed by molecular packing. Heating collagen at pHs below approximately 5, both Tm and Ts temperature will decrease.

Examination of solvent treated bone collagenous matrix shows that demineralized guanidine-extracted xenogenic bovine bone has a mixture of additional materials associated with it, and that extracting these materials plays a part in improving the biological properties of the matrices. The collagen of the matrix also may be deglycosylated.

Treatment of the matrix with a fibril modifying agent should be followed by an appropriate wash. Bone matrices that have been treated but left unwashed are generally less osteoinductive when implanted with osteogenic protein in a mammalian host. Panels A and B in FIG. 3 show the dramatic effect the wash step has on intraparticle surface area. Currently preferred washes include urea-containing buffer and water, or alternatively, a saline buffer.

Mammalian bone tissue growth requires the influx, proliferation and differentiation of migratory progenitor cells. Accordingly, in one aspect, the invention comprises packed matrix particles defining interstices dimensioned to permit the influx, proliferation and differentiation of migratory cells, preferably having a particle diameter that is in the range of 150–420 μm. The matrix particles also may be deglycosylated. The matrix comprises dispersed protein, e.g., osteogenic protein, and is capable of inducing endochondral bone formation when implanted in a mammalian host. Preferred means of adsorbing the substantially pure osteogenic protein onto the matrix particles include precipitation in cold ethanol from guanidine HCl solution, or incubation in an acetonitrile/trifluoroacetic acid solution or in PBS, followed by lyophilization. The matrix may be shaped to span a non-union fracture or to fill in a defect in bone of a mammalian host.

The biocompatible and in vivo biodegradable nature of the matrix also make it suitable for use as a delivery vehicle for the in vivo sustained release of therapeutic drugs. The increased porosity can increase the matrix's ability to trap and adsorb therapeutics. Moreover, it has been discovered that varying the treatment time, solvent concentration, and related treatment parameters can serve to alter the resorption rate of the matrix in vivo. Thus, this invention provides an easily generated carrier source material of great versatility. In view of this disclosure, those skilled in the art easily can create a carrier matrix having a specific, desired, reliable resorption time. They can then adsorb the agent of interest onto the matrix using one of the methods disclosed herein, or any of the techniques known in the art, to provide a sustained release vehicle with improved reliability in release of the therapeutic compound.

The particulate and porous nature of the material of this invention, along with its biocompatibility in mammalian hosts, permit its use at the interface of an implanted prosthetic device and the surrounding mammalian tissue to promote cellular ingrowth. Moreover, the matrix structure lends itself to increased durability during implantation when compared with the collagen fibrils commonly used in such compositions. In view of this disclosure, those skilled in the art easily can create a surface coating for prosthetic devices having a specific, predetermined porosity or micropitting and increased durability. They can then attach the coat to the prosthetic core using any of the techniques known in the art. See, for example, Cook et al., *Clin. Ortho. Rel. Res. No.* 232. p. 225, 1988. The matrix further can comprise osteogenic protein if endochondral bone induction is desired.

The nature of the matrix of this invention also makes it a superior substratum for in vitro growth of anchorage-dependent cells. The matrix itself provides a physiologically acceptable surface for cell attachment, and the particle interstices and intraparticle porosity and micropitting provides significant increases in the surface area available for cell attachment over other known matrices. A surface area on the order of 3000 $cm^2/$ g or higher can be achieved readily. Moreover, the structure of the matrix of this invention allows one to vary the particle porosity as desired. The cascade of pores present in this matrix promotes efficient nutrient access to cells, and increases the surface area available for cell attachment, thereby lowering the cell innoculant concentration required in a cell perfusion system (See GB 2,178,447). In view of this disclosure, one skilled in the art efficiently can create a biocompatible matrix of choice, having a specific, known, desired porosity or surface microtexture.

BRIEF DESCRIPTION OF THE DRAWINGS

The foregoing and other objects of this invention, the various features thereof, as well as the invention itself, may be more fully understood from the following description, when read together with accompanying drawings, in which.

DETAILED DESCRIPTION

Figure 1A:
FIGS. 1A through 1F are, respectively, scanning electron micrographs (<500X) of: (1A) Demineralized, guanidine-extracted rat bone matrix, (498X); (1B) Demineralized, guanidine-extracted bovine bone matrix, (480X); (1C) Demineralized, guanidine-extracted bovine bone matrix, further treated with hydrogen fluoride (HF), and washed, (350X); (1D) Demineralized, guanidine-extracted bovine bone matrix, further treated with 99.9% dichloromethane and 0.1% trifluoroacetic acid (DCM/TFA), and washed, (441X); (1E) Demineralized, guanidine-extracted bovine bone matrix, further treated with 99.9% acetonitrile and 0.1% trifluoroacetic acid (ACN/TFA), and washed, (429X); (1F) Demineralized, guanidine-extracted monkey bone matrix, further treated with hydrogen fluoride, and washed, (350X).

Practice of the invention requires the availability of bone, preferably mammalian bone, e.g., bovine. The bone is cleaned, demarrowed, delipidated, demineralized, reduced to particles of an appropriate size, extracted to remove soluble proteins, sterilized, and otherwise treated as disclosed herein to produce an implantable material useful in a variety of clinical settings.

Matrices of various shapes fabricated from the material of the invention may be implanted surgically for various purposes. Chief among these is to serve as a matrix for bone formation in various orthopedic, periodontal, and reconstructive procedures, as a sustained release carrier, or as a collagenous coating for implants. The matrix may be shaped as desired in anticipation of surgery or shaped by the physician or technician during surgery. Thus, the material may be used for topical, subcutaneous, intraperitoneal, or intramuscular implants; it may be shaped to span a nonunion fracture or to fill a bone defect. In bone formation or conduction procedures, the material is slowly absorbed by the body and is replaced by bone in the shape of or very nearly— the shape of the implant.

Various growth factors, hormones, enzymes, therapeutic compositions, antibiotics, and other body treating agents may be sorbed onto the carrier material and will be released over time when implanted as the matrix material is slowly absorbed. Thus, various known growth factors such as EGF, PDGF, IGF, FGF, TGF alpha, and TGF beta may be released in vivo. The material can be used to release antibiotics, chemotherapeutic agents, insulin, enzymes, or enzyme inhibitors.

Details of how to make and how to use the materials of the invention are disclosed below.

A. Preparation of Demineralized Bone

Demineralized bovine bone matrix is prepared by previously published procedures (Sampath and Reddi (1983) Proc. Natl. Acad. Sci. USA :80:6591-6595). Bovine diaphyseal bones (age 1-10 days) are obtained from a local slaughterhouse and used fresh. The bones are stripped of muscle and fat, cleaned of periosteum, demarrowed by pressure with cold water, dipped in cold absolute ethanol, and stored at $-20°$ C. They are then dried and fragmented by crushing and pulverized in a large mill. Care is taken to prevent heating by using liquid nitrogen. The pulverized bone is milled to a particle size in 70-850 $\mu$m, preferably 150 $\mu$m-420 $\mu$m, and is defatted by two washes of approximately two hours duration with three volumes of chloroform and methanol (3:1). The particulate bone is then washed with one volume of absolute ethanol and dried over one volume of anhydrous ether yielding defatted bone powder. The defatted bone powder is then demineralized by four successive treatments with 10 volumes of 0.5 N HCl at 4° C. for 40 min. Finally, neutralizing washes are done on the demineralized bone powder with a large volume of water.

B. Guanidine Extraction

Demineralized bone matrix thus prepared is extracted with 5 volumes of 4 M guanidine-HCl, 50mM Tris-HCl, pH 7.0 for 16 hr. at 4° C. The suspension is filtered. The insoluble material is collected and used to fabricate the matrix. The material is mostly collagenous in nature. It is devoid of osteogenic or chondrogenic activity.

C. Matrix Treatments

The major component of all bone matrices is Type-I collagen. In addition to collagen, demineralized bone extracted as disclosed above includes non-collagenous proteins which may account for 5% of its mass. In a xenogenic matrix, these noncollagenous components may present themselves as potent antigens, and may constitute immunogenic and/or inhibitory components. These components may also inhibit osteogenesis in allogenic implants by interfering with the developmental cascade of bone differentiation. The treatments described below use solvents to extract potentially unwanted components from the matrix, and use solvents or heat treatments to alter the surface structure of the matrix material.

After contact with the solvents, the treated matrix is washed to remove the extracted components, following a form of the procedure set forth below:

1. Suspend in TBS (Tris-buffered saline) 1g/200 ml and stir at 4° C. for 2 hrs; or in 6 M urea, 50 mM Tris-HCl, 500 mM NACl, pH 7.0 (UTBS) or water and stir at room temperature (RT) for 30 minutes (sufficient time to neutralize the pH);
2. Centrifuge and repeat wash step; and
3. Centrifuge; discard supernatant; water wash residue; and then lyophilize.

C1. Acid Treatments

1. Trifluoroacetic acid.

Trifluoroacetic acid is a strong non-oxidizing acid that is a known swelling agent for proteins which modifies collagen fibrils.

Bovine bone residue prepared as described above is sieved, and particles of the appropriate size are collected. These particles are extracted with various percentages (1.0% to 100%) of trifluoroacetic acid and water (v/v) at 0° C. or room temperature for 1-2 hours with constant stirring. The treated matrix is filtered, lyophilized, or washed with water/salt and then lyophilized.

2. Hydrogen Fluoride.

Like trifluoroacetic acid, hydrogen fluoride is a strong acid and swelling agent, and also is capable of altering intraparticle surface structure. Hydrogen fluoride is also a known deglycosylating agent. As such, HF may function to increase the osteogenic activity of these matrices by removing the antigenic carbohydrate content of any glycoproteins still associated with the matrix after guanidine extraction.

Bovine bone residue prepared as described above is sieved, and particles of the appropriate size are collected. The sample is dried in vacuo over $P_2O_5$, transferred to the reaction vessel and exposed to anhydrous hydrogen fluoride (10-20 ml/g of matrix) by distillation onto the sample at $-70°$ C. The vessel is allowed to warm to 0° C. and the reaction mixture is stirred at this temperature for 120 minutes. After evaporation of the hydrogen fluoride in vacuo the residue is dried thoroughly in vacuo over KOH pellets to remove any remaining traces of acid. Extent of deglycosylation can be determined from carbohydrate analysis of matrix sample taken before and after treatment with hydrogen fluoride, after washing the samples appropriately to remove non-covalently bound carbohydrates. SDS-extracted protein from HF-treated material is negative for carbohydrate as determined by CON A blotting.

The deglycosylated bone matrix is next washed twice in TBS (Tris-buffered saline) or UTBS, water-washed, and then lyophilized.

Other acid treatments are envisioned in addition to HF and TFA. TFA is a currently preferred acidifying reagent in these treatments because of its volatility. However, it is understood that other, potentially less caustic acids may be used, such as acetic or formic acid.

C2. Solvent Treatment

1. Dichloromethane.

Dichloromethane (DCM) is an organic solvent capable of denaturing proteins without affecting their primary structure. This swelling agent is a common reagent in automated peptide synthesis, and is used in washing steps to remove components.

Bovine bone residue, prepared as described above, is sieved, and particles of the appropriate size are incubated in 100% DCM or, preferably, 99.9% DCM/0.1% TFA. The matrix is incubated with the swelling agent for one or two hours at 0° C. or at room temperature. Alternatively, the matrix is treated with the agent many times (X3) with short washes (20 minutes each) with no—incubation.

Figure 4A:
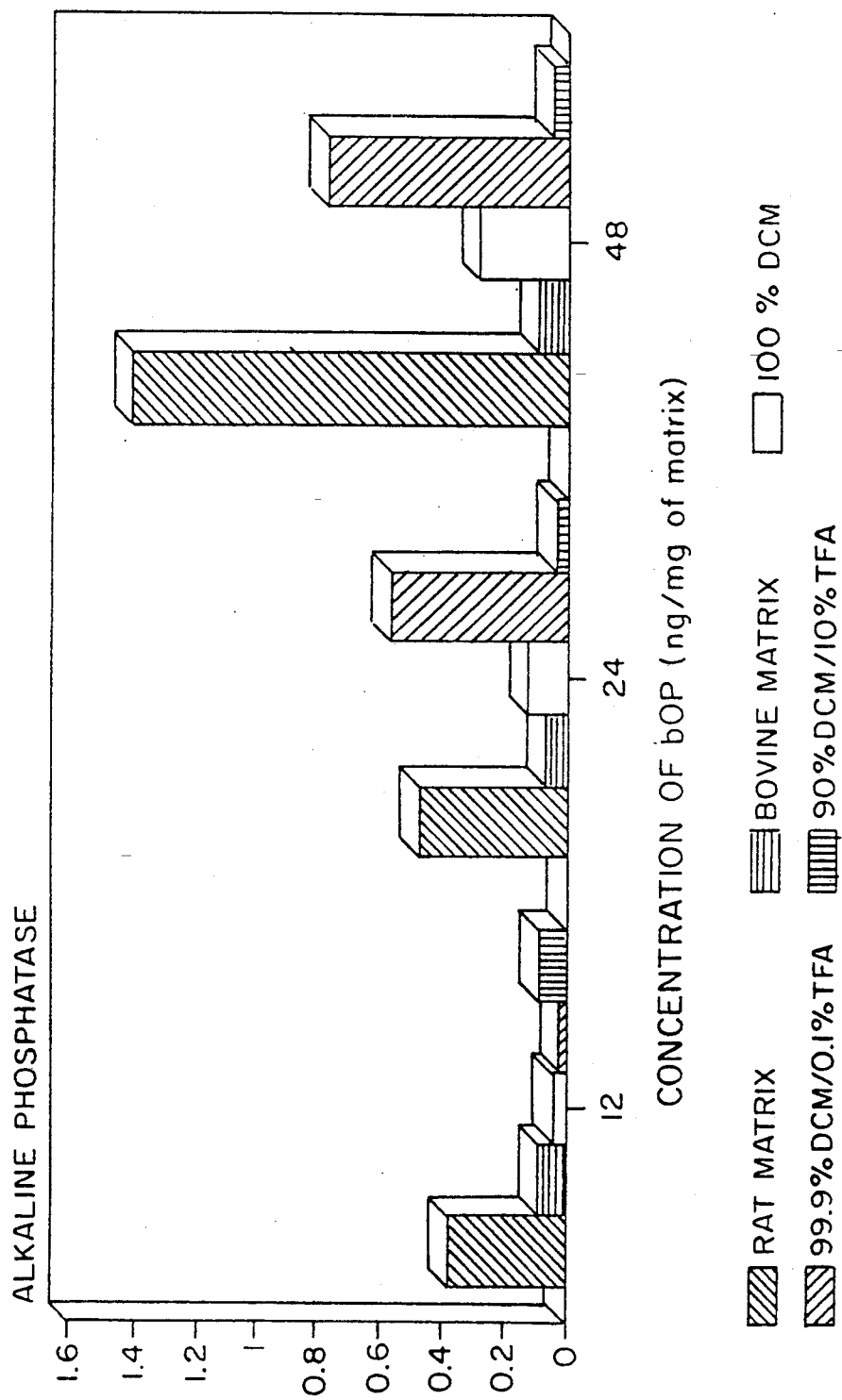
FIG. 4A is a bar graph of alkaline phosphatase activity as a measure of osteogenesis in the presence of variously-treated bovine bone matrix materials using DCM and DCM/TFA, and differing amounts of osteogenic protein.

FIG. 4A illustrates the effectiveness of the presence of a small amount of acid in an organic solvent swelling agent treatment in converting bovine matrix to a material useful as a bone formation matrix in rat.

2. Acetonitrile.

Acetonitrile (ACN) is an organic solvent, capable of denaturing proteins without affecting their primary structure. It is a common reagent used in high-performance liquid chromatography, and is used to elute proteins from silica-based columns by perturbing hydrophobic interactions.

Bovine bone residue particles of the appropriate size, prepared as described above, are treated with 100% ACN (1.0 g/30 ml) or, preferably, 99.9% ACN/0.1% TFA at room temperature for 1–2 hours with constant stirring. The treated matrix is then water-washed, or washed with urea buffer, or 4 M NACl and lyophilized. Alternatively, the ACN or ACN/TFA treated matrix may be lyophilized without wash.

3. Isopropanol.

Isopropanol is also an organic solvent capable of denaturing proteins without affecting their primary structure. It is a common reagent used to elute proteins from silica HPLC columns.

Bovine bone residue particles of the appropriate size prepared as described above are treated with 100% isopropanol (1.0 g/30 ml) or, preferably, in the presence of 0.1% TFA, at room temperature for 1–2 hours with constant stirring. The matrix is then water-washed or washed with urea buffer or 4 M NACl before being lyophilized.

4. Chloroform

Chloroform also may be used to increase surface area of bone matrix like the reagents set forth above, either alone or acidified.

Treatment as set forth above is effective to assure that the material is free of pathogens prior to implantation.

C3. Heat Treatment

Figure 4B:
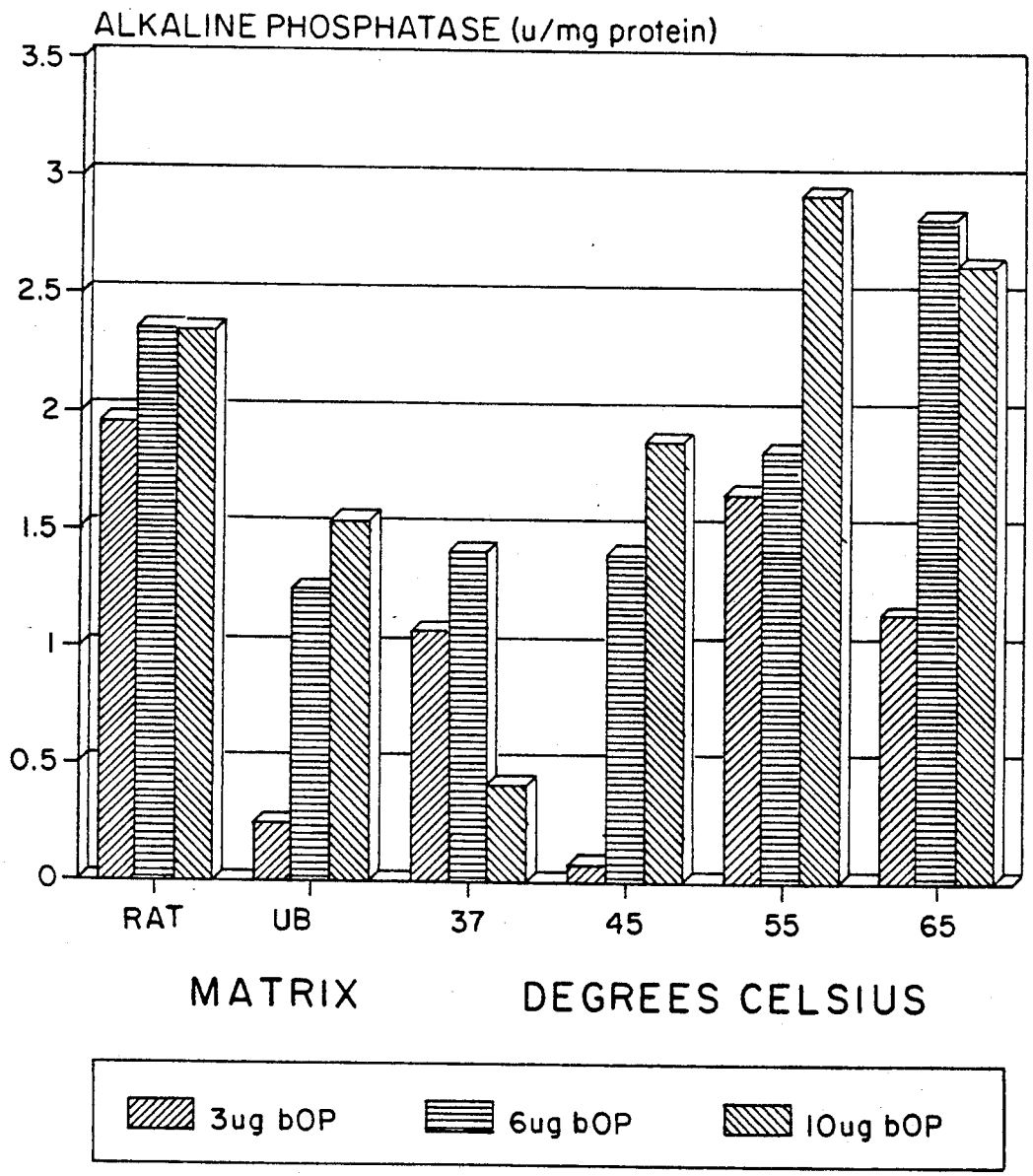
FIG. 4B is a bar graph of alkaline phosphatase activity as a measure of osteogenesis in the presence of temperature treated bovine bone matrix materials.
Figure 5A:
FIGS. 5A–5D are, respectively, scanning electron micrographs (approx. 1000X) of bovine matrix heat treated in water for one hour at (5A) 37° C, (5B) 45° C., (5C) 55° C., and (5D) 65° C. Compare FIG. 1B, untreated bovine matrix at 480X.
Figure 5B:
Figure 5C:
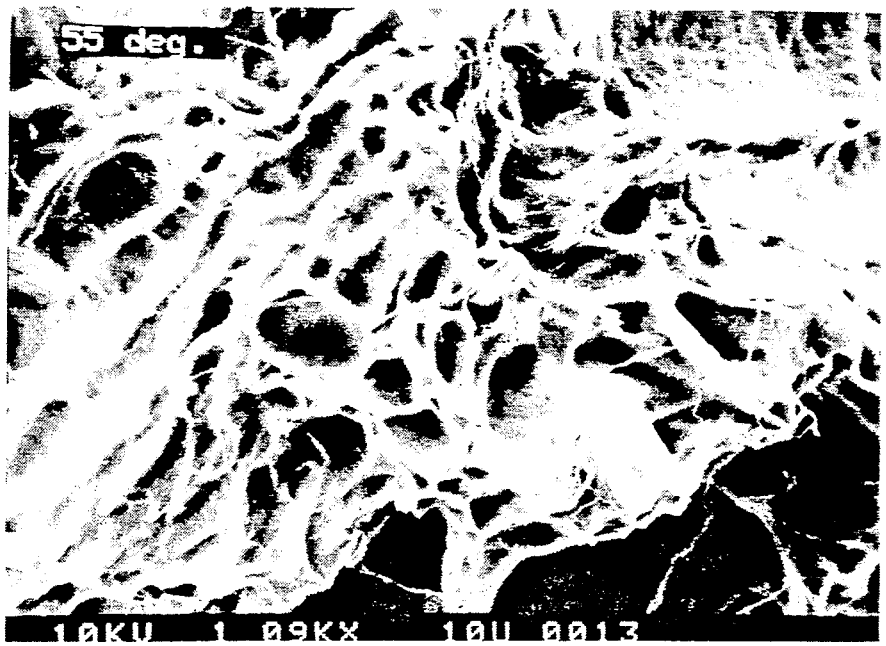
Figure 5D:

Various amounts of delipidated, demineralized guanidine-extracted bone collagen was heated in water (1g/30ml) under constant stirring in a glass flask, water jacketed, and maintained in a given temperature for 1 hour. In some instances the water is replaced with 0.1M acetic acid to help "swell" the collagen before heating. The temperature employed is held constant at room temperature, and about 37° C., 45° C., 55° C., 65° C., 75° C. After the heat treatment, the matrix is filtered and lyophilized and used for implant. The results are shown in FIG. 4B. FIG. 8 illustrates the morphology of the successfully altered collagen surface treated at 37° C., 45° C., 55° C. and 65° C.

The collagen matrix materials preferably take the form of a fine powder, insoluble in water, comprising nonadherent particles. It may be used simply by packing into the volume where new bone growth or sustained release is desired, held in place by surrounding tissue. Alternatively, the powder may be encapsulated in, e.g., a gelatin or polylactic acid coating, which is adsorbed readily by the body. The powder may be shaped to a volume of given dimensions and held in that shape by interadhering the particles using, for example, soluble, species biocompatible collagen. The material may also be produced in sheet, rod, bead, or other macroscopic shapes.

The functioning of the various matrices can be evaluated with an in vivo rat bioassay. Studies in rats show the osteogenic effect in an appropriate matrix to be dependent on the dose of osteogenic protein dispersed in the matrix. No activity is observed if the matrix is implanted alone. Demineralized, guanidine extracted xenogenic bone matrix materials of the type described in the literature are ineffective as a carrier, fail to induce bone, and produce an inflammatory and immunological response when implanted unless treated as disclosed above. Many of the allogenic matrix materials also are ineffective as carriers. The following sets forth various procedures for preparing osteogenic devices from control and matrix materials prepared as set forth above, and for evaluating their osteogenic utility.

A. Fabrication of Osteogenic Device

The osteogenic protein may be obtained using the methods disclosed in U.S. Pat. application Ser. No. 179,406 filed Apr. 8, 1988; PCT application No. US89/01469 (entitled Biosynthetic Osteogenic Proteins and Osteogenic Devices Containing Them), and PCT Application No. US89/01453, (entitled Osteogenic Devices). Both PCT applications were filed Apr. 7, 1989. Alternatively, extracts rich in osteogenic protein useful in fabricating devices may be obtained as disclosed in U.S. Pat. No. 4,294,753 to Urist. The disclosure of these documents is incorporated herein by reference.

A1. Ethanol Precipitation

Matrix is added to osteogenic protein dissolved in guanidine-HCl. Samples are vortexed and incubated at a low temperature. Samples are then further vortexed. Cold absolute ethanol is added to the mixture which is then stirred and incubated. After centrifugation (microfuge, high speed) the supernatant is discarded. The matrix is washed with cold concentrated ethanol in water and then lyophilized.

A2. Acetonitrile Trifluoroacetic Acid Lyophilization

In this procedure, osteogenic protein in an acetonitrile trifluroacetic acid (ACN/TFA) solution was added to the carrier material. Samples were vigorously vortexed many times and then lyophilized. Osteogenic protein was added in varying concentrations, and at several levels of purity. This method is currently preferred.

A3. Urea Lyophilization

For those osteogenic proteins that are prepared in urea buffer, the protein is mixed with the matrix material, vortexed many times, and then lyophilized. The lyophilized material may be used "as is" for implants.

A4. Buffered Saline Lyophilization

OP preparations in physiological saline may also be with the matrix and lyophilized to produce osteogenically active material.

These procedures also can be used to adsorb other active therapeutic drugs, hormones, and various bioactive species for sustained release purposes.

B. Implantation

The bioassay for bone induction as described by Sampath and Reddi (Proc. Natl. Acad. Sci. USA (1983) 80: 6591–6595), herein incorporated by reference, may be used to monitor endochondral bone differentiation activity. This assay consists of implanting the bovine test samples xenogenically in subcutaneous sites in recipient rats under ether anesthesia. Male Long-Evans rats, aged — 28–32 days, were used. A vertical incision (1 cm) is made under sterile conditions in the skin over the thoracic region, and a pocket is prepared by blunt dissection. Approximately 25 mg of the test sample is implanted deep into the pocket and the incision is closed with a metallic skin clip. The day of implantation is designated as day one of the experiment. Implants were removed on day 12. The heterotropic site allows for the study of bone induction without the possible ambiguities resulting from the use of orthotropic sites.

C. Cellular Events

Successful implants exhibit a controlled progression through the stages of matrix induced endochondral bone development including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartiliage calcification on day eight; (6) vascular invasion, appearance of osteoblasts, and formation of new bone on days nine and ten; (7) appearance of osteoblastic and bone remodeling and dissolution of the implanted matrix on days twelve to eighteen; and (8) hematopoietic bone marrow differentiation in the ossicle on day twenty-one. The results show that the shape of the new bone conforms to the shape of the implanted matrix.

D. Histological Evaluation

Histological sectioning and staining is preferred to determine the extent of osteogenesis in the implants. Implants are fixed in Bouins Solution, embedded in paraffin, and cut into 6-8 μμm sections. Staining with toluidine blue or hemotoxylin/eosin demonstrates clearly the ultimate development of endochondral bone. Twelve day implants are usually sufficient to determine whether the implants contain newly induced bone.

E. Biological Markers

Alkaline phosphatase activity may be used as a marker for osteogenesis. The enzyme activity may be determined spectrophotometrically after homogenization of the implant. The activity peaks at 9-10 days in vivo and thereafter slowly declines. Implants showing no bone development by histology have little or no alkaline phosphatase activity under these assay conditions. The assay is useful for quantitation and obtaining an estimate of bone formation quickly after the implants are removed from the rat. Alternatively, the amount of bone formation can be determined by measuring the calcium content of the implant.

F. Results

The histological evaluation of implants made using HF—, DCM—, DCM/TFA—, and ACN/TFA-treated bone matrices is given in Table 1 and in FIG. 4A. The osteogenic protein (OP) used in these experiments was isolated by the method disclosed in U.S. Pat. application Ser. No. 179,406. Experiments were performed using highly pure (C-18) protein. The results demonstrate unequivocally that xenogenic implants of collagenous bovine bone matrix treated as disclosed herein induces successful endochondral bone formation.

FIG. 4A illustrates the osteoinductive effect of water washed matrix treated with nanogram quantities of purified OP, as indicated by specific activity of alkaline phosphatase, for allogenic rat matrix and xenogenic bovine matrix untreated, treated with DCM alone, 99.9% DCM plus 0.1% TFA, and 90% DCM plus 10% TFA. As illustrated, DCM with low acidified concentrations of acid enhances bone formation.

Figure 2A:
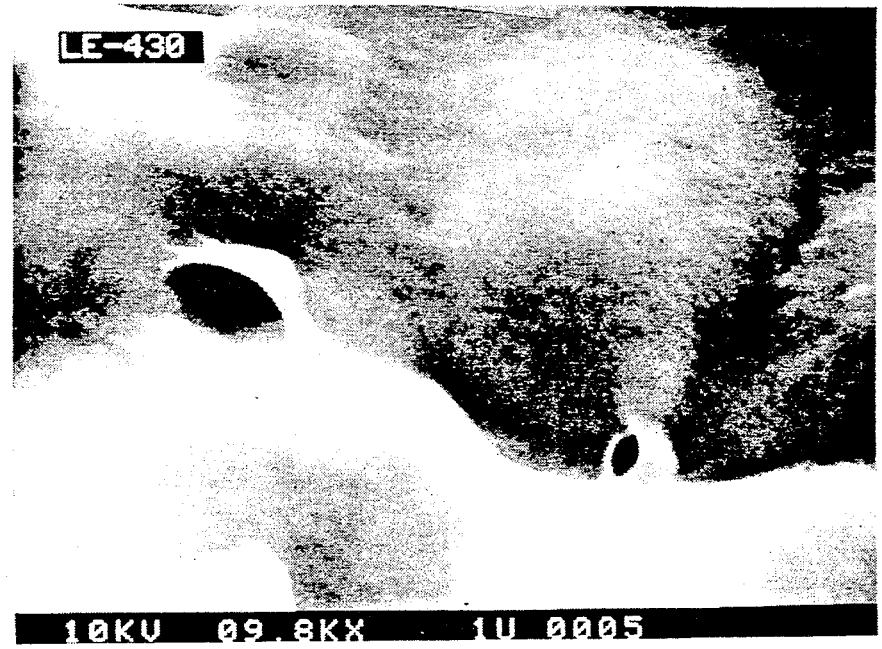
FIGS. 2A through 2E are respectively, Scanning electron micrographs ($\geq$5000X) of: (2A) Demineralized, guanidine-extracted rat bone matrix, (9800X); (2B) Demineralized, guanidine-extracted bovine bone matrix, (8700X); (2C) Demineralized, guanidine-extracted bovine bone matrix, further treated with hydrogen fluoride, and washed, (5000X); (2D) Demineralized, guanidine-extracted bovine bone matrix, further treated with DCM/TFA, and washed, (8000X); and (2E) Demineralized, guanidine-extracted bovine bone matrix, further treated with ACN/TFA, and washed, (11000X).
Figure 1B:
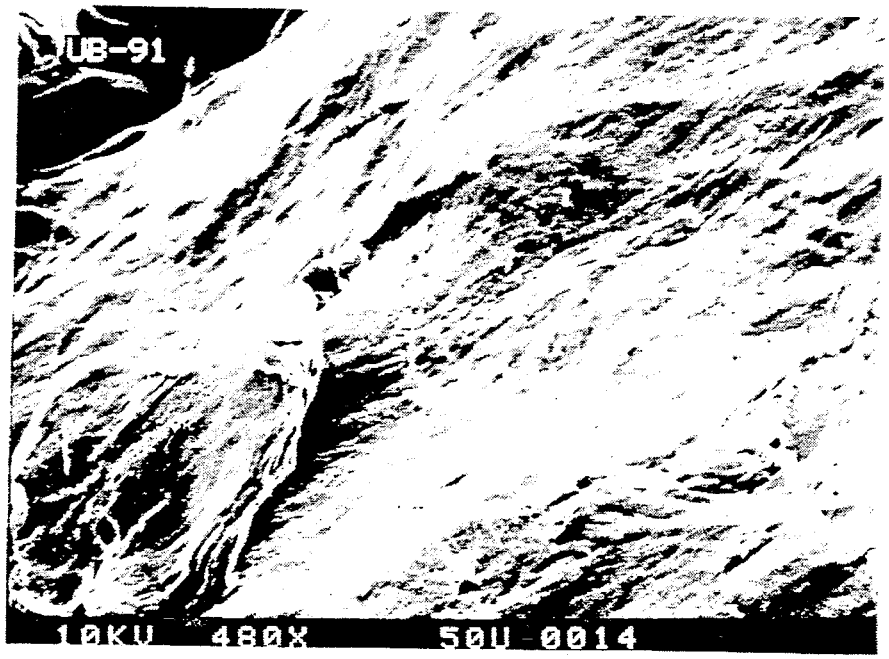
Figure 2B:
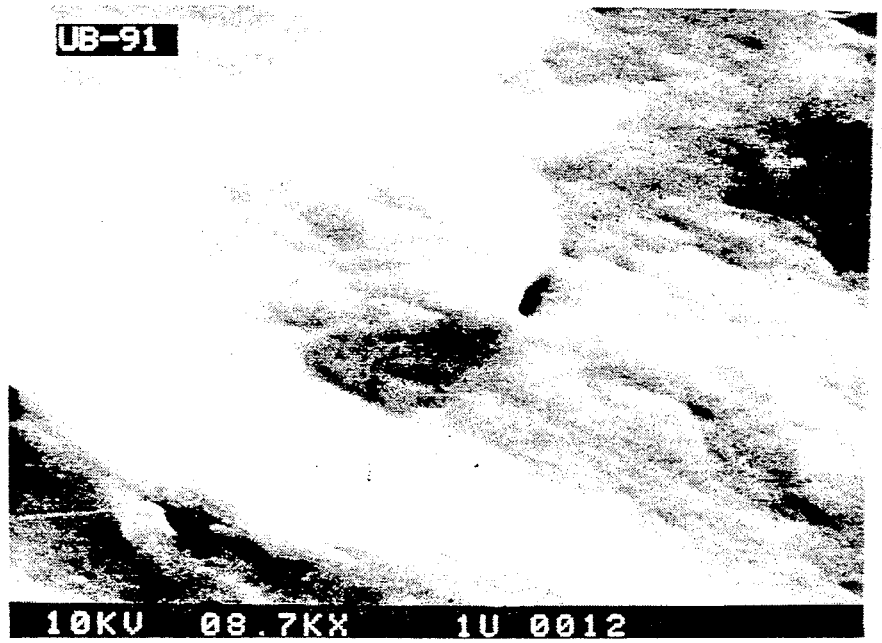
Figure 1C:
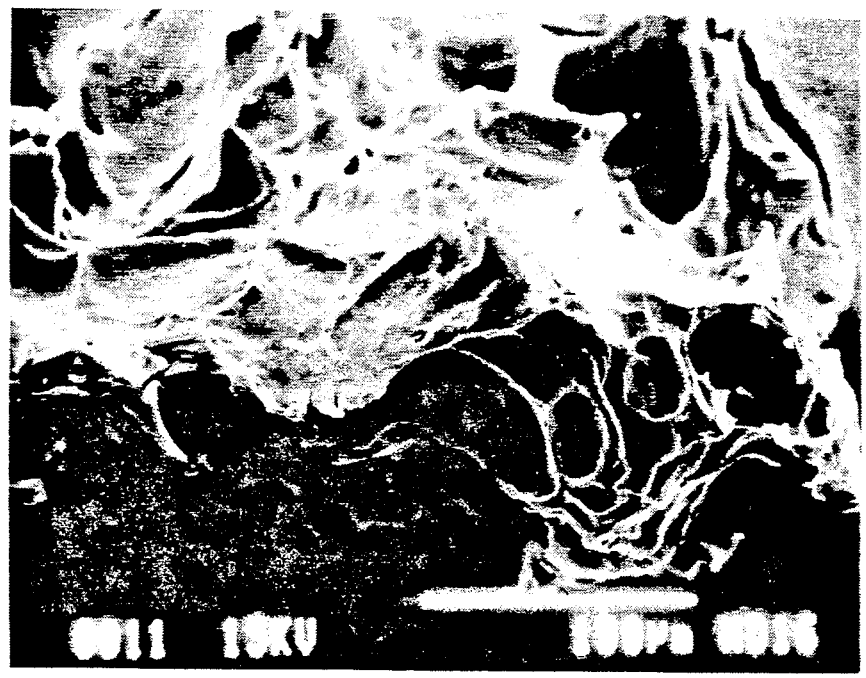
Figure 2C:
Figure 1D:
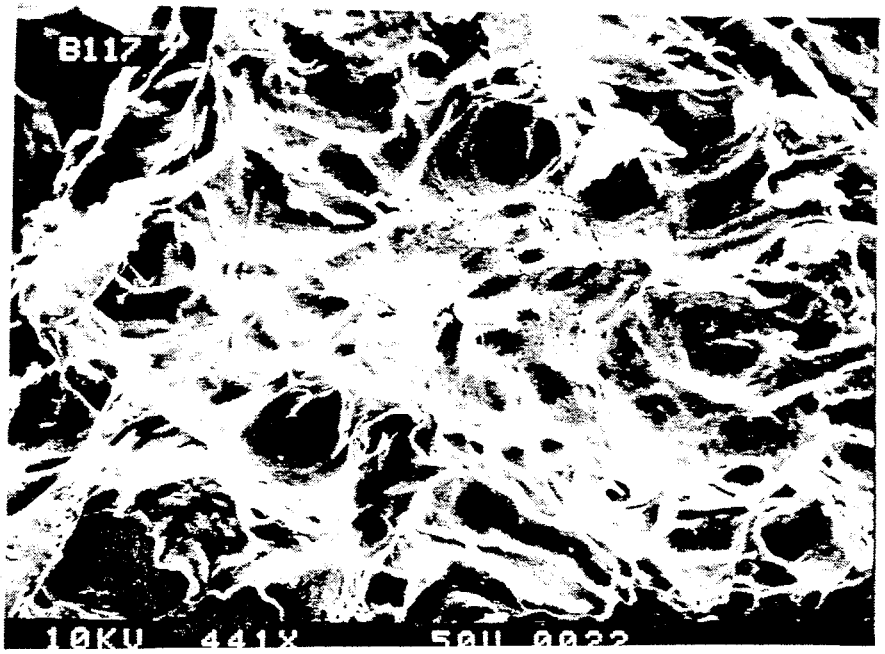
Figure 2D:
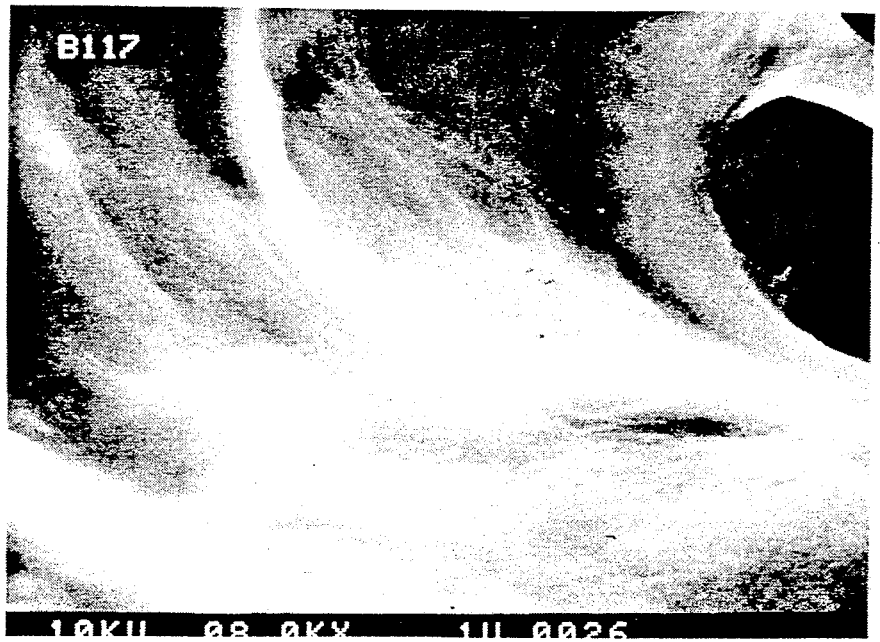
Figure 1E:
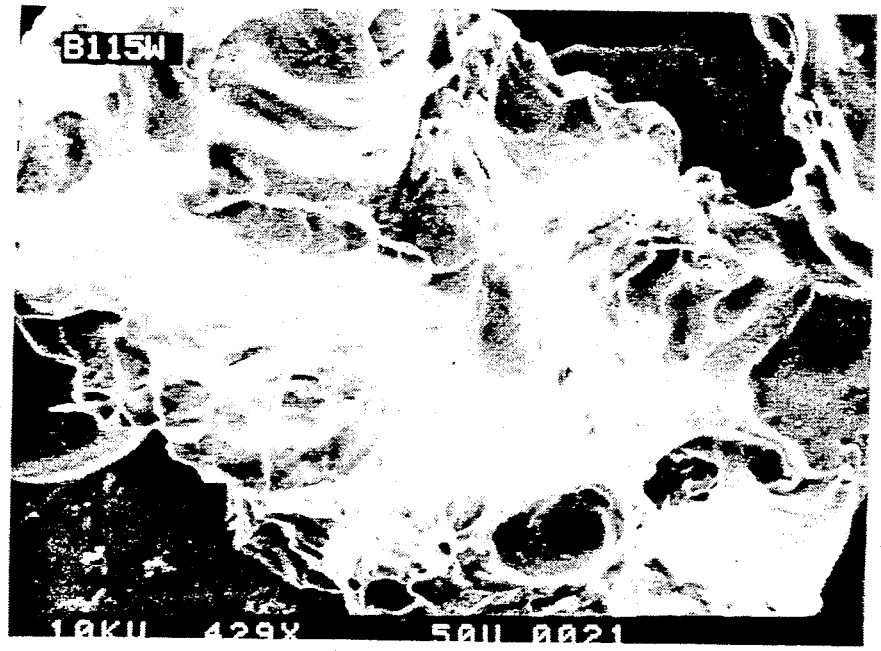
Figure 2E:

The utility of the material of the invention in its use as an osteogenic implant is believed to be dependent in part on increases in intraparticle surface area, including the formation of micropits and pores with the size range 1-100μm. The basis for this conclusion is apparent from a review and comparison of FIGURES 1A through 2E. Untreated rat matrix, shown in FIGURES 1A and 2A, is active in rats and has an obvious, open pore, high surface area structure. The untreated bovine matrix of FIG. 1B and 2B has a lower surface area and is inactive in rats. However, treatment of the bovine collagen with HF (FIGS. 1C and 2C), DCM/TFA (FIGURE 1D and 2D), or with ACN/TFA (FIG. 1E and 2E), produce an open pore, high surface area structure which is active xenogenically.

TABLE I

Osteogenic Activity in rat of treated bovine bone matrix, rat matrix, and untreated bovine matrix (25 mg matrix material per implant):

(Purified OP:)

| ng OP | Rat (untreated) | Bovine (untreated) | HF | DCM or ACN | DCM/ TFA | ACN/ TFA |
|---|---|---|---|---|---|---|
| 250 | ++ | — | +/− | + | + | + |
| 500 | +++ | — | + | ++ | ++ | ++ |
| 1000 | +++ | +/− | ++ | +++ | +++ | +++ |

Figure 1F:
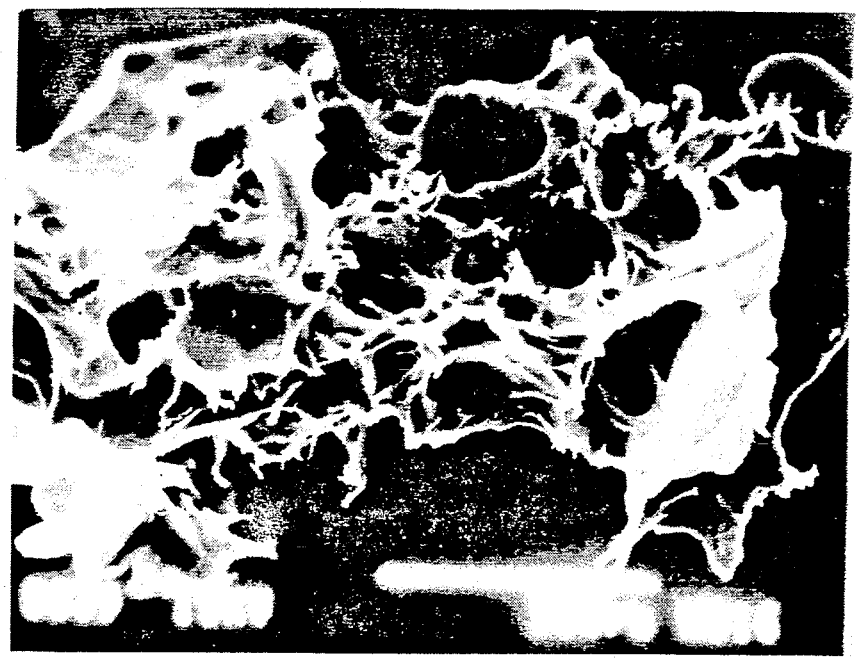
Figure 3A:
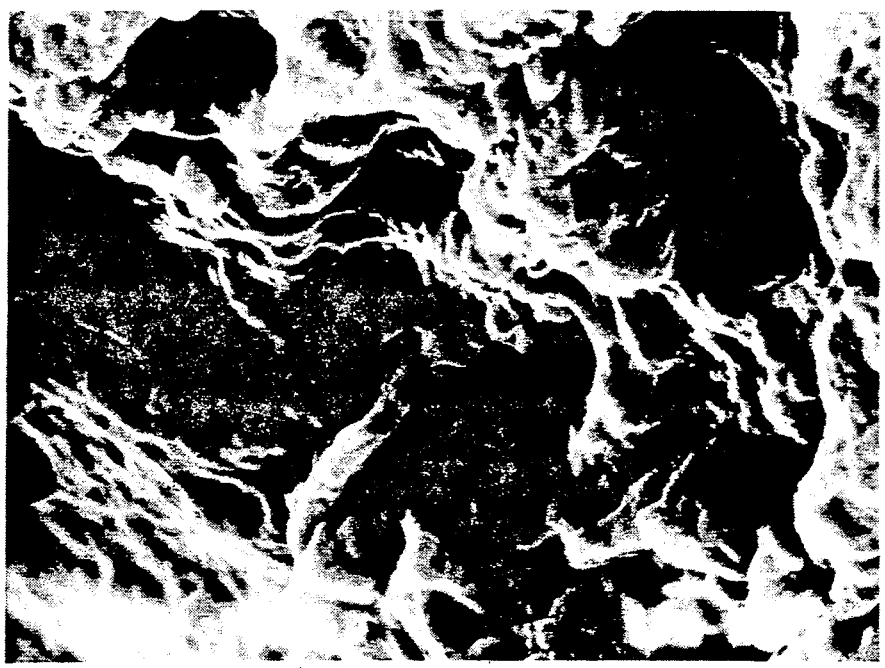
FIGS. 3A and 3B are, respectively, scanning electron micrographs (5000X) of: (3A) Demineralized, guanidine-extracted bovine bone matrix, further treated with dichloromethane, but not washed; and (3B) Demineralized, guanidine-extracted bovine bone matrix, further treated with dichloromethane, and washed.
Figure 3B:
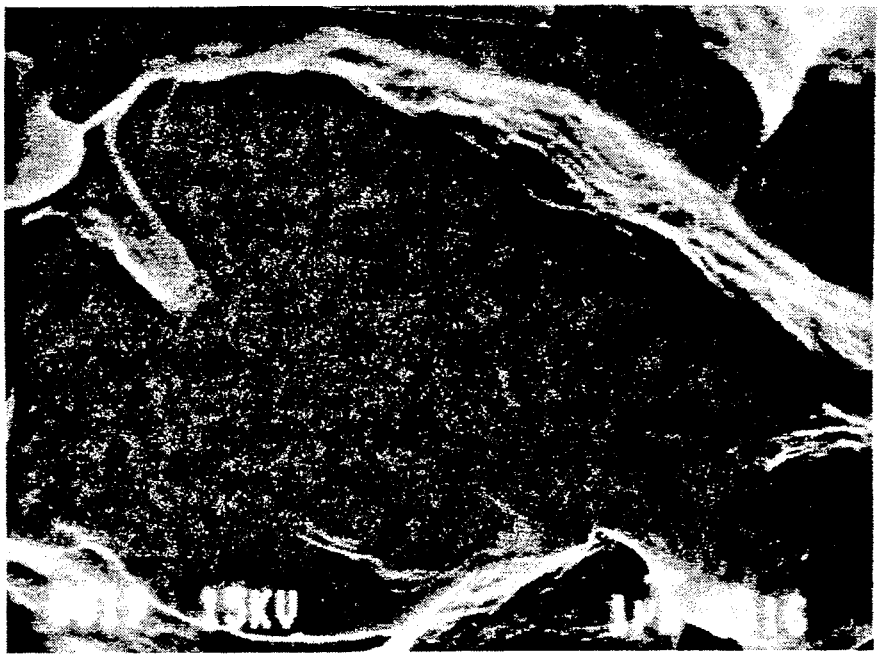

Histology score:
− no bone formation
+ slight bone formation
++ moderate bone formation
+++ extensive bone formation Pore number, average pore diameter, and total sur area as measured by intrusion volume, all are increased by the various treatments. Note the typical appearance of pores within pores and micropits within micropits resulting in an "oyster shell" appearance of the surface. FIG. 3 shows the appearance of bovine bone matrix particles when treated with DCM, with and without a subsequent wash step (3A and 3B, respectively). As illustrated, omission of the wash produces a low surface area structure similar to untreated bovine collagen, and results in an inactive matrix material. FIG. 1F shows the structure of monkey bone collagen after treatment with HF as disclosed above. The bone particles may be used xenogenically to induce bone. Demineralized, guanidine extracted monkey bone reportedly is ineffective as an osteogenic matrix, even as an allogenic implant.

A number of physical analyses were performed on the treated matrices as a means of corroborating the microscopic and physiological observations. Mercury porosimetry was used to compare the degree of porosity and deep micropitting of the various matrices. This standard method depends on the ability to intrude mercury into a material with incremental increases in applied pressure. In the case of an organic material such as treated bone matrix this pressure must be carried only to the point of bursting of the material or an error will be introduced skewing the pore diameter information towards the Angstrom level. The results of these experiments are shown in Table II and indicate that the treatment of bovine demineralized bone with collagen fibril modifying agents significantly increases the mercury intrusion volume, a parameter directly related to the increase in pore and deep micropit volume and area in the treated material, making this treated bovine matrix similar in intrusion volume to the active rat matrix material, and strongly corroborating the visual evidence of the scanning electron micrographs.

Specific surface area of each of the matrices was measured by the BET method using Krypton as the absorbate after outgassing of the material for 1 week at ambient temperature. Table II indicates that the treated bovine matrices have a significantly increased surface area when compared with untreated material, and are similar to the active rat matrix material, further corroborating the SEM data.

Skeletal density was measured for each of the materials by helium pycnometry and was found as would be expected to be about the same for each, so that one may conclude that the differences in bulk density as derived from mercury porosimetry data is attributable entirely to increase in surface area and porosity of the treated bovine matrices.

TABLE II

| Matrix | Intrusion Volume (Hg porosimetry) | Skeletal Density | Bulk Density | Surface Area (BET) | Pore Size (SEM) ($\mu$) |
|---|---|---|---|---|---|
| RAT | 2.525 | 1.340 | .278 | .3227 | 1-100 |
| UNTREATED BOVINE | 1.620 | 1.360 | .420 | .1566 | 0.01-10 |
| BOVINE ACN/TFA | 2.290 | 1.345 | .330 | .3160 | 1-100 |
| BOVINE ACN/TFA | 2.470 | 1.360 | .300 | .5724 | 1-100 |
| BOVINE DCM/TFA | 2.550 | 1.340 | .290 | .2242 | 1-100 |

An amino acid composition analysis has also been performed on the different matrices, in an effort to determine what effect, if any, the collagen fibril modifying agents have on non-collagenous protein associated with the matrix. The tyrosine content of the matrices is used as an indicator of noncollagenous protein, as the helical domain of collagen generally has only 2-3 tyrosine residues per 1000 residues. As indicated in Table III below, the treatments do not significantly affect the tyrosine (Y) content of the matrices, suggesting that the guanidine extracted bone collagen contained low concentrations of noncollagen proteins and the treatment fails to extract non-collagenous protein from the carrier matrix.

TABLE III

AMINO ACID ANALYSIS OF UNTREATED AND TREATED MATRIX[1]

| AA | 1 | 2 | 3 | 4 | 5 | 6 | 7 |
|---|---|---|---|---|---|---|---|
| D | 19 | 22 | 21 | 20 | 28 | 15 | 18 |
| E | 67 | 67 | 70 | 68 | 71 | 65 | 70 |
| S | 31 | 25 | 25 | 27 | 27 | 27 | 27 |
| G | 350 | 354 | 355 | 348 | 336 | 322 | 301 |
| H | 5 | 5 | 5 | 6 | 6 | 8 | 9 |
| R | 55 | 54 | 53 | 47 | 53 | 66 | 57 |
| T | 17 | 13 | 11 | 13 | 13 | 16 | 16 |
| A | 112 | 123 | 120 | 116 | 119 | 123 | 126 |
| P | 138 | 139 | 130 | 128 | 123 | 129 | 130 |
| HYP | 101 | 99 | 99 | 108 | 107 | 119 | 127 |
| Y | 5 | 4 | 5 | 5 | 6 | 5 | 6 |
| V | 26 | 26 | 27 | 26 | 27 | 28 | 30 |
| M | 3 | 1 | 2 | 1 | 2 | 3 | 2 |
| I | 11 | 11 | 12 | 11 | 12 | 11 | 12 |
| L | 24 | 23 | 27 | 26 | 28 | 23 | 25 |
| F | 16 | 14 | 25 | 15 | 15 | 16 | 17 |
| K | 21 | 23 | 23 | 23 | 23 | 25 | 27 |

[1]Expressed as residues/1000 residues
1) RAT MATRIX
2) UNTREATED BOVINE MATRIX
3) UNTREATED BOVINE MATRIX, UREA WASHED
4) 99.9% DCM/0.1% TFA BOVINE MATRIX, UREA WASH
5) 99.9% DCM/0.1% TFA BOVINE MATRIX, NO WASH
6) 99.9% ACN/0.1% TFA BOVINE MATRIX, NO WASH
7) 99.9% ACN/0.1% TFA BOVINE MATRIX, UREA WASH The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A matrix for implantation in a mammalian host comprising biodegradable, biocompatible, mineral-free delipidated Type-I insoluble bone collagen particles depleted in noncollagenous protein and treated to have an increased intraparticle porosity and surface area.

2. The matrix of claim 1 wherein said bone collagen is xenogenic to said host.

3. The matrix of claim 1 wherein the collagen is treated with a collagen fibril modifying agent.

4. The matrix of claim 1 wherein the collagen has an increased intrusion volume.

5. The matrix of claim 5 wherein the intrusion volume is increased by at least 25 percent.

6. The matrix of claim 4 wherein the intrusion volume is increased by at least about 50 percent.

7. The matrix of claim 1 wherein the collagen has an increased number of pores and micropits.

8. The matrix of claim 1 wherein the surface area of the collagen is at least doubled as measured by the BET method.

9. The matrix of claim 1 wherein the collagen has pores or micropits having a mean diameter within the range of 1$\mu$m-100$\mu$m.

10. The matrix of claim 7 wherein the number of pores and micropits is increased at least about threefold.

11. The matrix of claim 5 wherein the number of pores and micropits is increased at least about tenfold.

12. The matrix of claim 1 comprising packed particles having a mean diameter within the range of 70$\mu$m to 850$\mu$m.

13. The matrix of claim 1 comprising particles have a mean diameter within the range of 150$\mu$m to 420$\mu$m.

14. The matrix of claim 1 disposed on the surface of a synthetic bone replacement implant.

15. The matrix of claim 1 comprising interadhered particles defining interstices dimensioned to permit influx, proliferation and differentiation of migratory cells from the body of said mammalian host.

16. The matrix of claim 15 further comprising dispersed osteogenic protein, said matrix being capable of inducing endochondral bone formation when implanted in said mammalian host.

17. The matrix of claim 16 wherein said matrix is shaped to span a non-union fracture in said mammalian host.

18. The matrix of claim 1 further comprising a therapeutic drug adsorbed onto the surface thereof for sustained release in said mammalian host.

19. The matrix of claim 3 wherein said agent is dichloromethane.

20. The matrix of claim 3 wherein said agent is hydrogen fluoride.

21. The matrix of claim 3 wherein said agent is trifluoroacetic acid.

22. The matrix of claim 3 wherein said agent is dichloromethane, acetonitrile, or isopropanol mixed with 0.1%–10% trifluoroacetic acid.

23. The matrix of claim 3 wherein said agent is isopropanol.

24. The matrix of claim 3 wherein said agent is acetonitrile.

25. The matrix of claim 3 wherein said agent is chloroform.

26. The matrix of claim 3 wherein said agent is a hot aqueous medium.

27. The matrix of claim 26 wherein the medium has a temperature within the range of 37° C. to 65° C.

28. The matrix of claim 1 wherein said collagen is deglycosylated.

29. The matrix of claim 26 wherein said hot aqueous medium comprises 0.1M acetic acid.

* * * * *